United States Patent [19]

Gelabert

[11] Patent Number: 4,909,795
[45] Date of Patent: Mar. 20, 1990

[54] NON-REUSABLE SYRINGE

[76] Inventor: Danilo D. Gelabert, 7310 Standifer Gap Rd., Chattanooga, Tenn. 37421

[21] Appl. No.: 245,797

[22] Filed: Sep. 16, 1988

[51] Int. Cl.⁴ .............................................. A61M 5/32
[52] U.S. Cl. .................................... 604/198; 604/263; 604/110
[58] Field of Search ................. 604/192, 263, 187, 110

[56] References Cited

U.S. PATENT DOCUMENTS

| 2,708,438 | 5/1955 | Cohen | 604/192 |
| 4,009,716 | 3/1977 | Cohen | 604/192 |
| 4,735,311 | 4/1988 | Lowe et al. | 604/263 X |

FOREIGN PATENT DOCUMENTS 1385895 12/1964 France .................... 604/192

Primary Examiner—John D. Yasko
Attorney, Agent, or Firm—Alan Ruderman

[57] ABSTRACT

A non-reusable syringe has inner and outer barrels including a needle connected by a hub to the inner barrel and a plunger attached to the outer barrel and received within the inner barrel. A pair of circumferentially adjacent longitudinally extending tracks in the form of teeth are on the outer surface of the inner barrel and a traveler is fixed to the inner surface of the outer barrel, the teeth being such that the traveler may ride on each track in only one direction. One of the tracks is an outgoing or charging track which permits the outer barrel and the plunger to be drawn away from the needle end of the inner barrel to charge the inner barrel with injectable fluid. The other track is an incoming or discharge track permitting the traveler to ride in the direction toward the needle to permit the outer barrel and plunger to discharge fluid through the needle. The outer barrel may be rotated to move the traveler from the outgoing track to the incoming track, but the teeth on the outgoing track have a greater height than the teeth on the incoming track so that the traveler cannot move back onto the outgoing track. The hub has a flange including an inclined needle facing surface. A protective cap having a skirt at the open end may be disposed on the hub with the skirt removeably positioned on the flange. Another flange on the skirt has the same configuration as the flange on the hub, and after the use of the syringe the cap is pushed until the flanges lock thereby precluding removal of the cap.

11 Claims, 1 Drawing Sheet

NON-REUSABLE SYRINGE

BACKGROUND OF THE INVENTION

This invention relates to hypodermic syringes and more particularly to a hypodermic syringe assembly which can be used only once to load and discharge a fluid, the process of discharging acting to render the assembly non-usable, and to a lockable needle cap which may be locked over the needle after the syringe has been used.

With the increase of drug addiction by the intravenous injection of drugs in today's society, and the growth of certain health destroying diseases such as hepatitis and AIDS, which can be transmitted by the multiple use of syringes, it is highly desirable that hypodermic syringes be used only once and either destroyed or discarded in such a state that they are not reusable. Separate devices for destroying a syringe after use involves severing the needle and barrel components and results in the inconvenience of the additional acts of placing the syringe in the device and activating such device. If the syringe is not immediately destroyed in such a device but awaits personel to perform the act, the syringe may escape the normal procedure and be displaced before destruction can occur. Thus, a substantial number of non-reusable syringes have been proposed in the art in recent years.

In preparation for this application a preexamination patentability search was conducted and located the following U.S. Pat. Nos. 4,233,795 (Yerman); 4,391,272 (Staempfli); 4,713,056 (Butterfield); 4,731,068 (Hesse); 3,890,971 (Leeson et al); 4,650,468 (Jennings); 4,675,005 (DeLuccia); 4,687,467 (Cygielski); and 4,121,588 (Geiger).

In Yerman '975 there is a blocking member which is engaged by a plunger to close the fluid compartment after one use, the plunger not being connected to the blocking member so that on subsequent withdrawal of the plunger, the blocking member cannot be moved. In Staempfli '272 the plunger has a separable body which can move in one direction and thereafter lock and disconnect when the plunger is pulled back to the original position. In Hesse '068 there is a spider attached to a rod which is fastened to the plunger, the spider acting to pull a slidable sleeve rearwardly during the load stroke and to slip past the sleeve during the ejection stroke, the tips of the spider grasping the wall of the syringe thereafter to prevent further retraction of the plunger. In Butterfield '056 there is a latch ring which grasps the plunger head after the plunger has completed the ejection stroke thereby to prevent the plunger from again being retracted. In Jennings '468 the piston head housing is releasably locked to the syringe barrel and after injection it is unlocked by twisting and retracted together with the needle to the opposite end of the barrel where it is automatically locked against further use. In Leeson et al '971 there is a plunger and needle cap which may be permanently locked after use. In DeLuccia '005 there is a tool attached to the end of the plunger which can engage and withdraw the cannula and needle into the body of the syringe, and when in the body upon rotation, the rear of the piston can be threadedly locked to the closed end of the syringe body. Cygielski '467 has an internal cutter which punctures a hole in the needle end of the piston to prevent reuse, while Gieger '588 has a weakened zone for breaking of the barrel of the syringe.

One of the problems with all of the known prior art is that during the discharge portion of the cycle, if the plunger is not pushed far enough to inject all of the fluid through the syringe, the plunger may yet be pulled back and the syringe reused. Thus, if one who is using the syringe inadvertently does not push the plunger all the way during the discharge stroke, the syringes are not rendered inoperative.

SUMMARY OF THE INVENTION

Consequently, it is a primary object of the present invention to provide a syringe which may be used once to charge and discharge an injectable liquid and rendered non-reusable thereafter.

It is another object of the present invention to provide a disposable or non-reusable syringe wherein the plunger may be drawn away from the needle only once to load or charge the syringe and may be pushed toward the needle only once to discharge the syringe.

It is a further object of the present invention to provide a disposable or non-reusable syringe having an inner and outer barrel, the plunger being attached to and moveable with the outer barrel and disposed within the inner barrel, one of the barrels having a pair of longitudinally extending tracks and the other of the barrels having a traveler, the tracks being formed such that relative movement between the traveler and each track is possible in only one longitudinal direction, the relative movement being such that the outer barrel and the plunger may be drawn away from the needle to charge the inner barrel when the traveler is on one track, and thereafter upon relative rotation of the barrels, the traveler drops onto the other track to permit the plunger to be moved to discharge the inner barrel.

It is a still further object of the present invention to provide a syringe including a needle mounting hub having a cam flange on the periphery thereof spaced from the needle end, and a protective cap positionable on the hub, the cap having a skirt at the open end thereof for receiving the cam flange prior to use of the needle and removeable therefrom when the syringe is in use, the cap further including an annular cam adjacent the skirt adapted to cooperatively receive the cam flange when the skirt is forced over tee cam flange after the syringe has been used, but to preclude withdrawal of the cam flange therefrom.

Accordingly, the present invention provides a disposable non-reusable syringe having an inner and an outer barrel. A plunger is attached to the outer barrel and received within the inner barrel. A pair of circumferentially adjacent longitudinally extending tracks are formed on one of the barrels while a traveler is carried by the other of the barrels. The tracks are disposed such that the traveler may ride on each track in only one direction. Additionally, the tracks are disposed such that the plunger and the outer barrel may be drawn away from the needle during the charging or suction stroke as the traveler rides on a first of the tracks but relative movement between the traveler, and thus the plunger and outer barrel, and the first track cannot occur in the discharge direction. In order to discharge the syringe relative rotation between the barrels is required to switch the traveler to the second track where relative movement may occur as the traveler rides thereon during the discharge stroke. Once the traveler is on the second track, the plunger cannot be drawn in the direction of charging since relative movement between the traveler, and thus the plunger and outer barrel, and the second track cannot occur. Furthermore, the traveler is under compressive load while on the first track and the second track projects a smaller amount than the first track from the periphery of the barrel on which the tracks are formed so that after relative rotation to switch the traveler onto the second track, rotation back to the first track in the opposite direction is precluded while stop means are provided to preclude the traveler from rotating to a disposition where there is no track. Thus, relative rotational movement can only occur to position the traveler for movement from the first track to the second track and reuse of the syringe is precluded.

In the preferred form of the invention the tracks are disposed on the periphery of the inner barrel and the traveler and stop means are on the inner periphery of the outer barrel. The tracks in the preferred form of the invention each comprises a series of teeth, each tooth having a sloped surface over which the traveler may move and a step or riser at the trailing edge of the tooth so that the traveler may move over the surface of each tooth in the direction from the step at the trailing edge of the preceding tooth over the sloped surface. The surfaces of the teeth of the first track slope upwardly from the circumference of the inner barrel and in the direction remote from the needle, while the teeth of the second track slope in the opposite direction, the height of the teeth of the first track above the circumference of the inner barrel being greater than that of the second track. Stop means in the form of a protuberence extending from the inner circumference of the outer barrel substantially to the outer circumference of the inner barrel is disposed for abuting the first track when the traveler is disposed on the second track.

In accordance with another aspect of the present invention the needle for the syringe is fastened to a hub which includes a flange on the periphery thereof, the flange is in the form of a cam having a sloped surface at the needle facing end and a step at the opposite end. A protective cap having a correspondingly configured skirt at the open end thereof for positioning on the cam flange prior to use of the syringe is provided for protecting the needle. The cap also has an annular flange on its periphery spaced from the skirt, the flange having the same configuration as the cam flange on the hub. The cap may be readily removed from its protective position, and after use of the syringe, the cap is pushed over the hub until the flange on the hub is seated within the annular flange of the cap. Because of the sloped configuration, the cap cannot be removed from the hub and its protective condition with the needle.

BRIEF DESCRIPTION OF THE DRAWINGS

The particular features and advantages of the invention as well as other objects will become apparent from the following description taken in connection with the accompanying drawings, in which.

DESCRIPTION OF THE PREFERRED EMBODIMENTS

Figure 1:
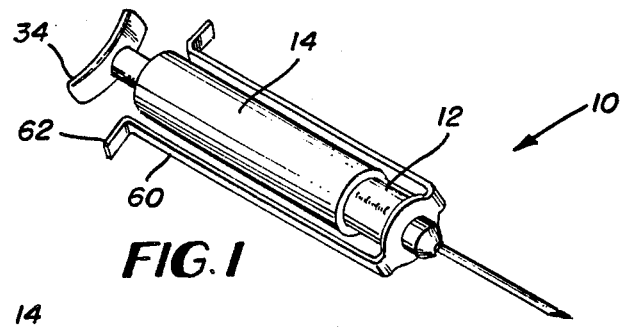
FIG. 1 is a perspective view of a syringe constructed in accordance with the principles of the present invention.

Referring now to the drawings, a syringe 10 constructed in accordance with the preferred embodiment of the present invention is disclosed as having an inner barrel 12 and an outer barrel 14, both barrels being of generally cylindrical form, and preferably constructed from appropriate thermoplastic material with at least the inner barrel being transparent.

The inner barrel 12 has a hollow interior which communicates with a hollow needle 16 at the forward end, the needle 16 being attached to a plastic hub 18 and either extending therethrough into communication with the interior of the barrel 12 or opening onto the hub 18 with the hub communicating with the interior of the barrel. In either case the hub may be fixed to or removeably attached to the front end 20 of the inner barrel 12 with the opposite end 22 of the inner barrel being open.

Figure 3:
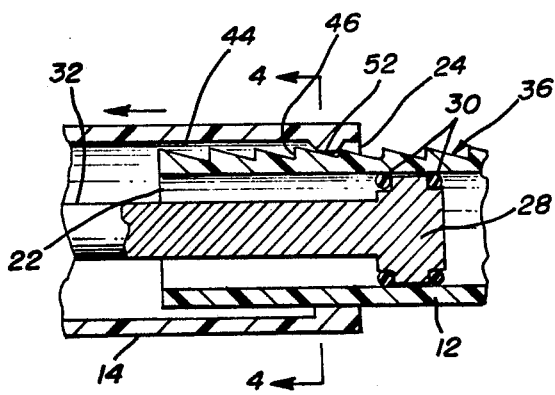
FIG. 3 is a fragmentary cross sectional view taken longitudinally through a portion of the assembled syringe.

The outer barrel 14 is open at its front end 24 and has a hollow interior of a diameter slightly larger than the outer diameter of the inner barrel 12, the rear end 26 of the barrel 14 being closed. The barrel 14 includes a plunger 28 mounted substantially concentric with the interior thereof and may extend from the front end 24. The plunger 28 is a substantially cylindrical member which may be of an elastomeric material or preferably is formed of a thermoplastic and includes elastomeric seals 30 which are compressively received within the hollow interior of the outer barrel 12 in sealed relationship with the interior wall thereof as illustrated in FIG. 3. Thus, the plunger 28 is disposed within the inner barrel 12 while the inner barrel is disposed within the outer barrel. The plunger 28 may be secured to the outer barrel 14 by means of a rod 32 attached at the rear face of the plunger and extending to the closed rear end 26 of the barrel 14. The rod 32 may extend through the rear end 26 which would then be closed about the extending portion, or another rod may extend from the rear face of the closed end 26. In either instance an operator or gripping member 34 is attached to the extending rod for drawing the outer barrel 14 and plunger 28 rearwardly relative to the inner barrel 12 during the charging stroke and for pushing the outer barrel 14 and plunger 28 forwardly during the discharge stroke as hereinafter described.

A pair of longitudinally extending tracks are disposed on or recessed from the outer periphery of the inner barrel or the inner periphery of the outer barrel while a traveler or track rider is disposed on the other of the barrels. In the preferred form of the invention, and for purposes of illustration, the tracks are disposed on the outer periphery of the inner barrel 12 while the traveler projects from the inner periphery of the outer barrel 14. Thus, tracks 36 and 38 extend longitudinally along the periphery of the barrel 12 and extend from adjacent the front end 20 to the rear end 22, the tracks 36 and 38 being circumferentially spaced apart but adjacent one another.

Figure 4:
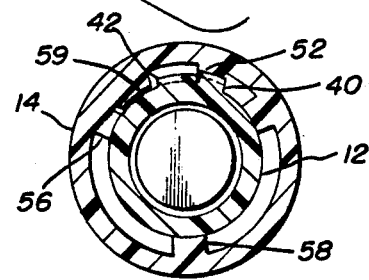
FIG. 4 is a cross sectional view taken substantially along line 4—4 of FIG. 3 illustrating the traveler on the first of the tracks.
Figure 6:
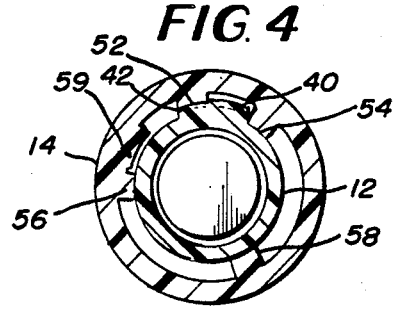
FIG. 6 is a perspective view of a protective cap for use with a syringe needle and showing the needle in phantom.
Figure 5:
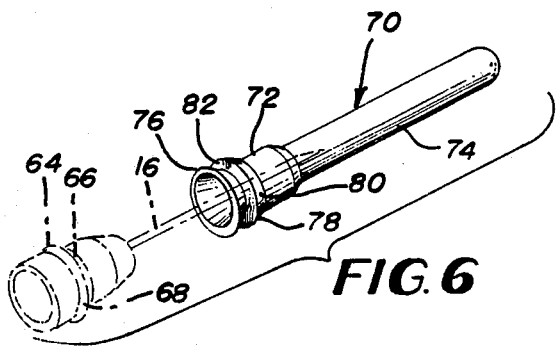
FIG. 5 is a view similar to FIG. 4 but illustrating the barrels rotated such that the traveler is on the second of the tracks.

The track 36 is the outgoing or charging track while the track 38 is the incoming or discharge track. As illustrated, each of the tracks 36, 38 comprise a series of teeth 40, 42 respectively extending substantially radially from the periphery of the barrel 12 with each of the teeth having a sloped surface and a step. The sloped surface 44 of the teeth 40 are inclined upwardly from the periphery of the barrel 12 in the direction from the front end 20 toward the rear end 22, and each tooth 40 has a step or riser 46 at the trailing end thereof which drops downwardly toward the periphery of the barrel 12 at which point the adjacent tooth commences. Thus, the teeth 40 are effectively detents providing a one-way rack or ratchet bar. The teeth 42 of the track 38 are also one-way rack or ratchets but, on the other hand, has the sloped surface 48 inclined upwardly from the periphery of the barrel in the direction from the rear end 22 toward the front end 20 with each step or riser 50 also at the trailing end, the trailing end in this case being at the front of the barrel. Thus, the risers 46 of the teeth 40 face the rear end of the barrel 12, while the risers 50 of the teeth 42 face the front end 20 of the barrel 12. Additionally, the height of the teeth 42 above the periphery of the barrel 12 is less than the height of the teeth 40, as best illustrated in FIGS. 4 and 5, for purposes which will hereinafter become clear.

Disposed within the barrel 14 on the inner wall thereof at the front end is a traveler in the form of a protuberance 52. The traveler 52 projects radially inwardly toward the center of the barrel 14 by an amount such that it engages the sloped surface 48 of the teeth 42 at the radially innermost portion thereof, i.e., the edge of the teeth 42 which abut the riser 50 at the trailing edge. The traveler may thus ride over the teeth 42 on the discharge stroke readily without stress thereof, and when initially positioned on the teeth 40, as hereinafter described, the traveler will be stressed in compression, as may the teeth 40 and the barrel 12. Also formed on the inner wall of the barrel 14 is an abutment or stop member 54 also in the form of a radially extending protuberance, the abutment member 54 being disposed such that the outer barrel 14 may be rotated relative to the inner barrel 12 when the traveler is disposed on the teeth 40 of the track 36 in the direction to move the traveler onto the track 38, e.g., counter-clockwise as illustrated in FIG. 4, but once the traveler is on the teeth 42 of the track 38, rotation in that same direction is precluded by the abutment member 54 acting against the teeth 40 of the track 36, as illustrated in FIG. 5. Thus, the traveler may be switched from track 36 to track 38, but cannot be switched from track 38 to track 36. At least one and preferably two other protuberances 56, 58 extend radially from the interior wall of the outer barrel 14 for maintaining concentric alignment of the barrels 12 and 14.

Figure 2:
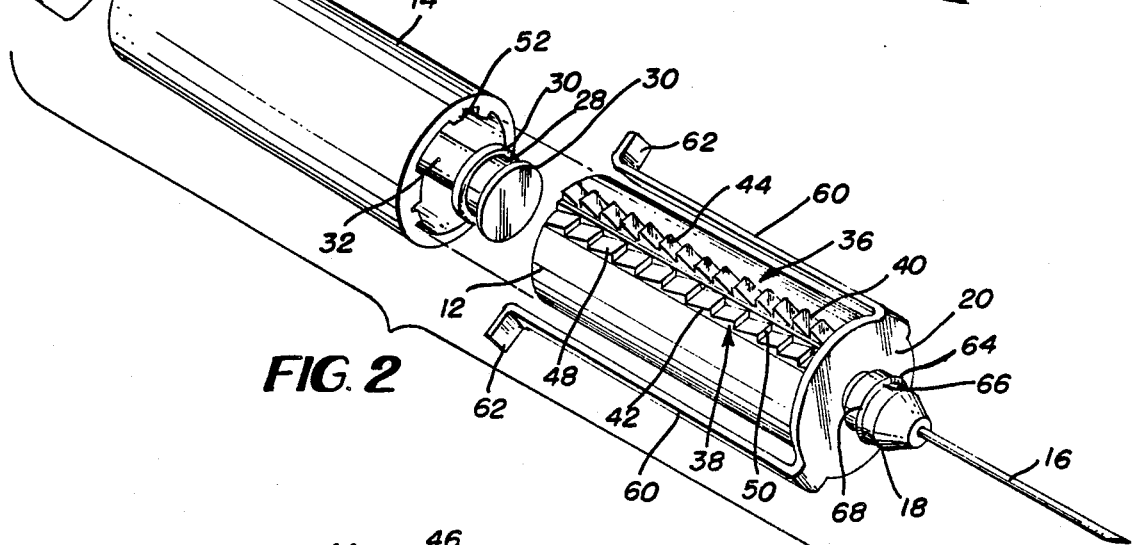
FIG. 2 is an exploded perspective view of the syringe illustrated in FIG. 1 showing the major components thereof.

As illustrated in FIG. 2, the teeth 40 and 42 of the respective tracks 36 and 38 are offset slightly from each other. Additionally, an assembly stop boss 59 extends from the interior wall of the outer barrel 14, the assembly boss being circumferentially spaced from the traveler 52 in the direction in which the traveler is to be moved from the track 36 onto the track 38, i.e., counter-clockwise as illustrated in FIGS. 4 and 5. The circumferential disposition of the traveler 52, the stop member 54 and the assembly stop boss 59 is such that the outer barrel 14 may be positioned about the inner barrel 12 during initial assembly with the assembly stop boss 59 disposed on the teeth 42 of the low track 38 so that the traveler is disposed adjacent the teeth 40 of the high track 36 on the remote side of the track 38. The assembly stop boss protrudes from the outer barrel an amount such that it compresses the teeth 42 of the track 36 when so positioned thereon, i.e., there is a preloading force applied by the assembly stop boss on the teeth 42. The assembly stop boss 59 prevents relative rotation of the barrels 12, 14 in the direction opposite to the direction the traveler must be moved to enter onto the track 38 from the track 36, e.g., the clockwise direction as illustrated in FIGS. 4 and 5. The outer barrel may then be pushed in relatively to the inner barrel 12 with the assembly stop boss riding on the teeth 42 of the low track, and with the traveler moving freely. When the plunger 28 is then seated adjacent the wall 20 of the closed end of the inner barrel 12, the traveler is adjacent the lower portion of the slope 44 of the first tooth 40, i.e., the tooth 40 most adjacent the front wall 20. The barrels 12, 14 may then be relatively rotated slightly until the traveler 52 is disposed on the first tooth 40 of the high track 36, and the assembly stop boss 59 is at that time displaced from the low track 38 on the side thereof remote from the track 36 as illustrated in FIG. 4. The assembly boss thereafter prevents the barrels from rotating in the direction which would dislodge the traveler from the high track 36 toward the remote side of the track 38, e.g., clockwise as illustrated in FIGS. 4 and 5. If desired or found necessary, a protuberance or enlargement may be placed in the front of the tooth 42 adjacent that front tooth 40 so that the relative rotation of the barrels is limited to ensure that the traveler stops on and does not overshoot the tooth 40 of the charging track. Once so positioned the syringe is ready for use.

A pair of elongated limbs 60 extending at opposed circumferential portions of the front wall of the barrel 12 have respective grasping flanges 62, the limbs 60 being disposed about the outer barrel 14 when assembled so that the flanges 62 aid in the pulling back and subsequent pushing forward of the outer barrel 14 relative to the inner barrel 12.

In operation, the inner barrel may be charged by pulling back on the gripping member 34. As the outer barrel 14 moves rearwardly by means of the pulling of the gripping member 34, the traveler rides over the teeth 40 of the track 36, the traveler, teeth 40 and inner barrel 12 being in a compressed state as the traveler rides over the sloped surface. Whenever the traveler reaches a step 46, forward movement of the outer barrel 14 relative to the inner barrel 12 is thereafter precluded. When the traveler reaches the location where the inner barrel is charged with the desired amount of injectable fluid due to the suction created by the plunger 28, the grasping member 34 is turned slightly to rotate the outer barrel relative to the inner barrel until the stop member 54 engages the track 36 and the traveler is switched to and positioned on a tooth 42 of the track 38. The outer barrel 14 and the plunger 28 are then pushed forward relative to the inner barrel 12 as the traveler rides over the teeth 42 until the fluid has been discharged from the syringe. Rotation of the outer barrel back in the opposite direction to the track 36 is thereafter precluded by reason of the teeth 40 of the track 36 being higher than the teeth 42 of the track 38, and the outer barrel is precluded from rotation in the originally moved direction by reason of the abutting relationship of the stop member 54 against the track 36. Thus, further use of the syringe is precluded.

In accordance with a second aspect of the present invention, the needle hub 18, which may be removably attached to the syringe body by conventional means such as threads or the like, has a flange 64 extending radially outwardly from the surface thereof. The flange 64 may extend continuously about the circumference of the hub as illustrated or there merely may be a pair of diametrically opposed flanges extending therefrom. The flange 64 has a forward facing sloped surface 66 which slopes outwardly and radially so that the rear of the flange is at the greatest extent from the surface of the hub, thereby forming a sharp step 68 at the rear of the flange 64. A protective cap 70 having an enlarged diametric portion 72 for fitting over the hub 18 and an elongated narrow smaller diameter portion 74 for fitting about the needle in protective conventional manner is provided, the cap 70 having a first annular flange or skirt 76 adapted to receive the entire flange 64 of the hub 18. The skirt 76 has the same configuration as the flange 64 and may be positioned snugly thereon prior to use and may be removeable therefrom by pulling the cap forwardly when the syringe is ready for use. The cap 70 also has another annular flange 78 spaced from the skirt 76, the flange 78 being of the same configuration as the flange 64 on the hub. Thus, the annular flange 78 has a sloped surface 80 sloping upwardly and rearwardly from the surface of the portion 72 to a point where it has a sharp drop or step 82. After use of the syringe, the cap is pushed rearwardly over the needle 16 and the hub 18 until the flange 64 is received within the annular flange 78 and the steps 68 and 82 abut. Thereafter, the cap 70 is locked to the hub 18 since the steps preclude removal of the cap from the hub. Accordingly, access to the needle is prevented, whether or not the needle hub is separatable from the syringe body.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A disposable syringe comprising an axially elongated hollow interior inner barrel having an open end and a closed end, a hollow needle, needle connecting means for attaching said needle to said closed end of said barrel with the interior of said needle communicating with the interior of said barrel, an axially elongated hollow interior outer barrel having an open end and a closed end, said inner barrel being disposed within said outer barrel with the interior surface of said outer barrel facing the exterior surface of said inner barrel, a plunger extending axially within said outer barrel and moveable therewith, said plunger being disposed within and forming a seal with the interior of said inner barrel, first and second longitudinally extending circumferentially adjacent tracks formed on one of said inner and outer surfaces, a traveler formed on the other of the inner and outer surfaces and adapted for riding on said tracks, said first track being disposed for permitting said traveler to ride thereon in a first direction extending from the closed end to the open end of said inner barrel but precluding said traveler from riding thereon in a second direction opposite said first direction, said second track being disposed for permitting said traveler to ride thereon in said second direction extending from the open end to the closed end of said inner barrel but precluding said traveler from riding thereon in said first direction, and abutment means for permitting said outer barrel to rotate relative to said inner barrel in a direction permitting said traveler to switch from said first track to said second track but for precluding switching of said traveler from said second track to said first track, whereby said outer barrel and plunger may be drawn in said first direction to charge said inner barrel with injectable fluid while said traveler is on said first track and may be rotated to switch said traveler to said second track for permitting said outer barrel and plunger to thereafter move in said second direction to discharge said fluid.

2. A disposable syringe as recited in claim 1, wherein said first and second tracks each comprise a series of ratchet teeth, and said traveler comprises a protuberence.

3. A disposable syringe as recited in claim 1, wherein said plunger is fixed to said outer barrel.

4. A disposable syringe as recited in claim 1, wherein said tracks are disposed on the outer surface of said inner barrel and said traveler comprises a protuberence on the inner surface of said outer barrel.

5. A disposable syringe as recited in claim 4, wherein said first and second track each comprises a series of teeth, the teeth of said first track being angularly inclined in a direction extending in said first direction and outwardly relatively to the outer surface of said inner barrel, and the teeth of said second track being angularly inclined in a direction extending in said second direction and outwardly relatively to the outer surface of said inner barrel, and adjacent teeth of each track forming a step from the outermost portion of one tooth to the innermost portion of an adjacent tooth.

6. A disposable syringe as recited in claim 5, wherein the teeth of said first track extend a greater amount than the teeth of said second track relatively to the outer surface of said inner barrel, and said abutment means includes wall portions of the teeth of said first track adjacent said second track.

7. A disposable syringe as recited in claim 6, wherein said abutment means further comprises a protuberence on the inner surface of said outer barrel disposed adjacent at least one tooth of said first track remote from said second track and for abutting said at least one tooth after the traveler is on the second track and further rotation of the outer barrel is attempted in the direction permitting the traveler to switch from the first track to the second track.

8. A disposable syringe as recited in claim 7, wherein said plunger is fixed to said outer barrel.

9. A disposable syringe as recited in claim 1, wherein said needle connecting means comprises a hub secured to said closed end, said hub having a front end and a peripheral surface intermediate said front end and said closed end, a flange extending outwardly from said peripheral surface, said flange having a wall substantially normal to said surface facing said closed end and a forward facing wall inclined relative to said surface, and a protective cap adapted to be disposed on said hub in a protective position over said needle, said cap having an annular skirt at one end thereof for receiving and being removeably attached to said flange when said cap is positioned on said hub, said cap further including an annular locking flange formed on said cap spaced from said skirt, said locking flange having substantially the same configuration and size as the flange on said hub for receiving and locking about the flange on said hub when said cap pushed toward said closed end and said skirt is forced past the flange on said hub.

10. A disposable syringe comprising a barrel having a hollow interior, a first end and a second end, a plunger extending through said first end and slidably disposed within said hollow interior, a hollow needle, a hub connected to said needle and to said second end for attaching said needle to said barrel with the interior of said needle in flow communication with the interior of said barrel, said hub having a peripheral surface intermediate said second end and said needle, a flange extending outwardly from said peripheral surface, said flange having a wall substantially normal to said surface facing said second end sand a forward facing wall inclined relative to said surface converging in a direction toward said needle, a protective cap having a closed end and an open end adapted to be disposed on said hub in a protective position over said needle, said cap having an annular skirt at said open end having an inclined interior surface converging toward said closed end for snugly receiving and being removeably attached to said forward facing wall of said flange when said cap is positioned on said hub, and an annular locking flange formed on said cap spaced from said skirt, said locking flange having an internal configuration of substantially the same configuration and size as the flange on said hub for receiving and locking about the flange on said hub when said cap is pushed toward said closed end and said skirt is forced past the flange on said hub.

11. The combination of a needle and a protective cap for use with a syringe having a barrel including a hollow interior, a first end and a second end, a plunger extending through said first end and slidably disposed within said hollow interior, said needle having a hollow interior, a hub secured to said needle and connected to said second end for attaching said needle to said barrel with the interior of said needle in flow communication with the interior of said barrel, said hub having a peripheral surface intermediate said second end and said needle, a flange extending outwardly from said peripheral surface, said flange having a wall substantially normal to said surface facing said second end and a forward facing wall inclined relative to said surface converging in a direction toward said needle, said protective cap having a closed end and an open end adapted to be disposed on said hub in a protective position over said needle, said cap having an annular skirt at said open end having an inclined interior surface converging toward said closed end for snugly receiving and being removeably attached to said forward facing wall of said flange when said cap is positioned on said hub, and an annular locking flange formed on said cap spaced from said skirt, said locking flange having an internal configuration of substantially the same configuration and size as the flange on said hub for receiving and locking about the flange on said hub when said cap is pushed toward said closed end and said skirt is force past the flange on said hub.

* * * * *